United States Patent
Oxman et al.

(10) Patent No.: US 6,620,405 B2
(45) Date of Patent: Sep. 16, 2003

(54) DELIVERY OF HYDROGEL COMPOSITIONS AS A FINE MIST

(75) Inventors: Joel D. Oxman, Minneapolis, MN (US); Sumita B. Mitra, West St. Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 10/001,251

(22) Filed: Nov. 1, 2001

(65) Prior Publication Data

US 2003/0103911 A1 Jun. 5, 2003

(51) Int. Cl.[7] ............................ A61K 7/16; A61K 7/18; A61K 7/20
(52) U.S. Cl. .......................... 424/45; 424/49; 424/52; 424/53; 433/215; 433/216
(58) Field of Search ................ 424/45, 49, 58; 239/237–239; 433/215, 216

(56) References Cited

U.S. PATENT DOCUMENTS

| | | |
|---|---|---|
| 3,639,574 A | 2/1972 | Schmolka et al. |
| 3,652,420 A | 3/1972 | Hill |
| 4,011,309 A | 3/1977 | Lutz |
| 4,066,566 A | 1/1978 | Lauster |
| 4,100,271 A | 7/1978 | Krezanoski |
| 4,116,239 A * | 9/1978 | Ewen ........................ 128/184 |
| 4,130,501 A | 12/1978 | Lutz et al. |
| 4,188,373 A | 2/1980 | Krezanoski |
| 4,474,751 A | 10/1984 | Haslam et al. |
| 4,474,752 A | 10/1984 | Haslam et al. |
| 4,537,778 A | 8/1985 | Clipper et al. |
| 4,696,757 A | 9/1987 | Blank et al. |
| 4,719,149 A | 1/1988 | Aasen et al. |
| 4,770,634 A | 9/1988 | Pellico |
| 4,774,093 A | 9/1988 | Provenchee et al. |
| 4,795,527 A | 1/1989 | Cohen |
| 4,829,996 A * | 5/1989 | Noakes et al. ............... 239/706 |
| 4,839,156 A | 6/1989 | Ng et al. |
| 4,861,760 A | 8/1989 | Manzuel et al. |
| 4,888,168 A | 12/1989 | Potts et al. |
| 4,921,626 A | 5/1990 | Rhodenbaugh |
| 4,952,212 A * | 8/1990 | Booth et al. ................. 604/294 |
| 4,962,868 A * | 10/1990 | Borchard ...................... 222/49 |
| 4,978,336 A * | 12/1990 | Capozzi et al. ............. 239/398 |
| 4,980,152 A | 12/1990 | Frazier et al. |
| 5,000,955 A | 3/1991 | Gould et al. |
| 5,053,000 A * | 10/1991 | Booth et al. ................... 604/20 |
| 5,057,308 A | 10/1991 | Hill et al. |
| 5,057,309 A | 10/1991 | Hill et al. |
| 5,057,310 A | 10/1991 | Hill et al. |
| 5,059,417 A | 10/1991 | Williams et al. |
| 5,061,183 A | 10/1991 | Nicholson |
| 5,071,637 A | 12/1991 | Pellico |
| 5,073,363 A | 12/1991 | Pellico |
| 5,077,033 A | 12/1991 | Viegas et al. |

(List continued on next page.)

FOREIGN PATENT DOCUMENTS

| | | |
|---|---|---|
| EP | 102 200 A2 | 3/1984 |
| EP | 288 420 B1 | 10/1988 |
| EP | 325 267 B1 | 7/1989 |

(List continued on next page.)

OTHER PUBLICATIONS

BASF Product Literature, "BASF Performance Chemicals Pluronic® & Tetronic® Surfactants," BASF Corporation (1996).

(List continued on next page.)

Primary Examiner—Shep K. Rose
(74) Attorney, Agent, or Firm—Doreen S. L. Gwin

(57) ABSTRACT

Dental compositions are provided that can be delivered as a fine mist and that have the capability of undergoing an increase in viscosity in response to an increase in temperature. In a preferred embodiment, the compositions also have the ability to reverse their viscosity in response to a decrease in temperature.

18 Claims, 1 Drawing Sheet

U.S. PATENT DOCUMENTS

Figure 1:
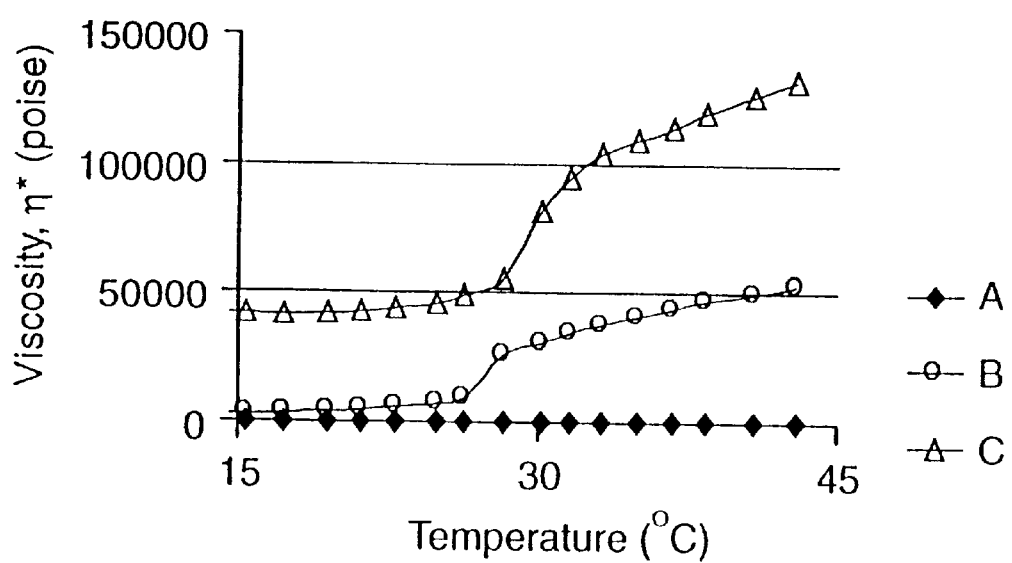

| | | | |
|---|---|---|---|
| 5,078,129 A | | 1/1992 | Kleinberg et al. |
| 5,098,303 A | | 3/1992 | Fischer |
| 5,116,315 A | * | 5/1992 | Capozzi et al. ............... 604/82 |
| 5,122,365 A | | 6/1992 | Murayama |
| 5,124,151 A | | 6/1992 | Viegas et al. |
| 5,171,564 A | | 12/1992 | Nathoo et al. |
| 5,234,342 A | | 8/1993 | Fischer |
| 5,252,318 A | | 10/1993 | Joshi et al. |
| 5,256,065 A | | 10/1993 | Nicholson |
| 5,256,396 A | | 10/1993 | Piechota, Jr. |
| 5,277,175 A | * | 1/1994 | Riggs et al. ........... 128/200.21 |
| 5,300,295 A | | 4/1994 | Viegas et al. |
| 5,340,613 A | | 8/1994 | Hanzalik et al. |
| 5,374,396 A | * | 12/1994 | Blackford et al. ............. 422/73 |
| 5,376,006 A | | 12/1994 | Fischer |
| 5,376,693 A | | 12/1994 | Viegas et al. |
| 5,376,695 A | | 12/1994 | Schmidt |
| 5,378,542 A | | 1/1995 | Hanzalik et al. |
| 5,401,495 A | | 3/1995 | Murayama |
| 5,409,630 A | | 4/1995 | Lysy et al. |
| 5,409,631 A | | 4/1995 | Fischer |
| 5,441,732 A | | 8/1995 | Hoeg et al. |
| 5,492,937 A | | 2/1996 | Bogentoft et al. |
| 5,575,652 A | | 11/1996 | Gaffar et al. |
| 5,631,000 A | | 5/1997 | Pellico et al. |
| 5,718,886 A | | 2/1998 | Pellico |
| 5,725,843 A | | 3/1998 | Fischer |
| 5,746,598 A | | 5/1998 | Fischer |
| 5,766,012 A | | 6/1998 | Rosenbaum et al. |
| 5,766,574 A | | 6/1998 | Christina-Beck et al. |
| 5,770,105 A | | 6/1998 | Fischer |
| 5,814,304 A | | 9/1998 | Wong et al. |
| 5,819,988 A | | 10/1998 | Sawhney et al. |
| 5,846,570 A | | 12/1998 | Barrow et al. |
| 5,847,023 A | | 12/1998 | Viegas et al. |
| 5,851,514 A | | 12/1998 | Hassan et al. |
| 5,861,148 A | | 1/1999 | Smith |
| 5,902,568 A | | 5/1999 | Ryles et al. |
| 5,928,628 A | | 7/1999 | Pellico |
| 6,116,900 A | | 9/2000 | Ostler |
| 6,126,443 A | | 10/2000 | Burgio |
| 6,312,666 B1 | * | 11/2001 | Oxman et al. ............... 438/215 |
| 6,312,667 B1 | * | 11/2001 | Trom et al. ................... 433/215 |
| 6,350,123 B1 | * | 2/2002 | Rizoiu et al. .................. 433/80 |

FOREIGN PATENT DOCUMENTS

| | | |
|---|---|---|
| EP | 535 816 A2 | 4/1993 |
| EP | 545 594 B1 | 6/1993 |
| EP | 612 512 A2 | 8/1994 |
| EP | 758 544 A2 | 2/1997 |
| GB | 1 571 832 | 7/1980 |
| GB | 2 170 406 A | 8/1986 |
| JP | 59 128330 A | 7/1984 |
| WO | WO 91/14650 A1 | 10/1981 |
| WO | WO 86/00813 A1 | 2/1986 |
| WO | WO 96/02276 A2 | 2/1996 |
| WO | WO 96/02577 A1 | 2/1996 |
| WO | WO 96/06134 A1 | 2/1996 |
| WO | WO 96/25457 A1 | 8/1996 |
| WO | WO 96/28056 A1 | 9/1996 |
| WO | WO 97/00275 A2 | 1/1997 |
| WO | WO 97/11675 A1 | 4/1997 |
| WO | WO 98/30494 A1 | 7/1998 |
| WO | WO 99/11208 | 3/1999 |
| WO | WO 99/32135 | 7/1999 |
| WO | WO 00/28946 A1 | 5/2000 |
| WO | WO 00/28955 A1 | 5/2000 |
| WO | WO 00/47203 | 8/2000 |
| WO | WO 02/41837 | 5/2002 |

OTHER PUBLICATIONS

"Buyer's Guide to Whitening Systems," *Dentistry Today*, pp. 125–134 (Dec., 1997).

"Den–Mat," product information sheets [on–line]. Den–Mat Corporation, Santa Maria, CA, 1998–1999 [retrieved on Mar. 13, 2000]. Retrieved from the Internet: <URL:http://www.denmat.com/main/htm>; 10 pgs.

"Discuss Dental product information sheets for Professional Whitening Products," [on–line]. Discuss Dental [retrieved on Mar. 13, 2000]. Retrieved from the Internet: <URL:http://www.discusdental.com/>; 13 pgs.

Haywood et al., "Nightguard Vital Bleaching," *Quintessence International*, vol. 20, No. 3, pp. 173–176 (1989).

"Surfactants, Pluronic & Tetronic," BASF product information brochure, Mount Olive, NJ, 40 pages (1999).

"Timoptic–XE® (Timolol Maleate Ophthalmic Gel Forming Solution)," product literature (instructions for use), Merck & CO., Inc., West Point, PA, issued Jun., 1999. 6 pgs.

"The Innovative Company Behind *Rembrandt Products*," product information sheets [on–line]. Den–Mat Corporation, Santa Maria, CA, 1998–1999 [retrieved on Mar. 13, 2000]. Retrieved from the Internet: <URL:http://www.rembrandt-.com/denmat/about.htm> 14 pgs.

"Ultradent Online Materials and Procedures Manual," [on–line]. Ultradent Products, Inc., 1999 [retrieved on Mar. 13, 2000]. Retrieved from the Internet: <URL:http://www.ultradent.com/>; 20 pgs.

* cited by examiner

DELIVERY OF HYDROGEL COMPOSITIONS AS A FINE MIST

FIELD OF THE INVENTION

This invention relates to the delivery as a fine mist of dental treatment compositions having viscosities capable of responding to a change in temperature. The invention also relates to devices for applying the compositions as a fine mist.

BACKGROUND

In the dental art, the use of a dental treatment composition is generally desirable for numerous applications or indications including, for example, treatment of caries, calculus build-up, xerostomia, stained dentition, bad breath, gingivitis, bacterial infections, oral pain or sensitivity such as sore throat, canker sores, and burns. To attain proper application and effectiveness at the desired location, it is desirable that the composition be controllable and slow to flow away from it target site. Thus a high viscosity dental composition in the oral environment would be quite useful.

Currently available dental compositions are provided in seemingly extreme viscosity states. That is, there exist compositions that have very low viscosities as well as compositions that are highly thickened and therefore possess high viscosity. Those with low viscosities are difficult to control and have tendencies to flow away from the target site once it is applied. Compositions with high viscosities are difficult to extrude through a small orifice.

Certain dental compositions may use thickeners such as fumed silica and/or polymer additives such as polyvinyl alcohols, polyethylene glycols, and the like. Problems encountered in using these thickeners include aging, which results in non-homogenous gels which make handling difficult, and shear thinning, which reduces the viscosity of a gel when extruded through an orifice and thinning at elevated temperatures. Thinning can result in a material that drips from the desired point of application.

Dental etching compositions, which are suitable for etching hard tissue and include an acid and a thermally responsive viscosity modifier, are disclosed in PCT International Publication No. WO 00/28946. Dental whitening compositions that include a whitening agent and a thermally responsive viscosity modifier are disclosed in PCT International Publication No. WO 00/28955. Such compositions are capable of being applied to a target site through an orifice (e.g., a syringe), whereupon they undergo an increase in viscosity in response to an increase in temperature. The increase in viscosity is useful in preventing the dental compositions from flowing away from the target area of application.

There exists a need in the art for convenient methods of delivering dental compositions to target sites, and for the compositions to remain at the target application area after delivery.

SUMMARY OF THE INVENTION

In one aspect, the present invention provides a method of applying a dental composition in the oral environment using an aqueous dental composition including about 10% by weight to about 50% by weight of a thermally responsive viscosity modifier and water, wherein the composition is in a low viscosity state at a pre-treatment temperature and a highly viscous state at a treatment temperature that is higher than the pre-treatment temperature. The method includes spraying the composition as a fine mist onto a surface, wherein the composition is at the pretreatment temperature and in the low viscosity state prior to being sprayed onto the surface, allowing the composition to warm to the treatment temperature and increase in viscosity to the highly viscous state wherein the viscosity of the composition at the treatment temperature is at least about 10 times the viscosity of the composition at the pre-treatment temperature, and allowing the composition to remain on the surface. Preferably the pre-treatment temperature at most about room temperature and the treatment temperature is about body temperature. The dental composition may optionally include adjuvants such as acids, whitening agents, fluoride sources, stability promotors, anti-microbial agents, anti-fungal agents, anti-calculus forming agents, preservatives, adhesive modifiers, fillers, dyes, detection indicators (e.g., for caries, gingivitis, and the like), cariostatic agents, flavorings, sweeteners, medicaments, sodium bicarbonate, specific enzymes, hydrating agents, and breath fresheners. The dental composition optionally may also include a propellant.

In another aspect, the present invention provides a spray device including a container; an aqueous dental composition in the container, the composition including about 10% by weight to about 50% by weight of a thermally responsive viscosity modifier and water, wherein the composition is in a low viscosity state at a pre-treatment temperature and a highly viscous state at a treatment temperature that is higher than the pre-treatment temperature; and a sprayer in fluid communication with the dental composition, the device being capable of spraying the dental composition as a fine mist into the oral environment. Optionally, the device may further include a propellant.

In another aspect, the present invention provides a fine mist of a dental composition in the oral environment, the composition including about 10% by weight to about 50% by weight of a thermally responsive viscosity modifier and water, wherein the composition is in a low viscosity state at a pre-treatment temperature and a highly viscous state at a treatment temperature that is higher than the pre-treatment temperature.

In another aspect, the present invention provides a dental composition capable of being sprayed as a fine mist into the oral environment, the composition including about 10% by weight to about 50% by weight of a thermally responsive viscosity modifier; water; and a propellant, wherein the composition is in a low viscosity state at a pre-treatment temperature and a highly viscous state at a treatment temperature that is higher than the pre-treatment temperature.

BRIEF DESCRIPTION OF THE DRAWINGS

FIG. 1 is a graphic illustration of the viscosity versus temperature data as described in Preparative Example 3.

DETAILED DESCRIPTION OF THE PREFERRED EMBODIMENTS

The present invention provides a dental composition in a low viscosity state prior to application onto an oral surface, but which also is highly viscous, thick and controllable at the target site. These compositions are easily dispensed, applied, and manipulated when handled by the user, and are easily controlled upon application to the target site. Because the composition has a low viscosity initially at a pre-treatment temperature, it is easily delivered as a fine mist to the intended site. In addition, production of low viscosity compositions may provide easier processing and greater uniformity and consistency.

Compositions of this invention are particularly suitable for use in the intraoral environment where a composition having a pre-treatment temperature at or lower than ambient (room temperature) is applied to a user's oral surface that is near or at oral temperature of about 30° C. to about 39° C. For certain dental applications, it is preferred that the composition be thermally reversible. In that application, the composition not only has the ability to increase its viscosity at an elevated intra-oral temperature, but also reverses or decreases its viscosity upon a decrease in temperature.

The capacity of the dental composition to thicken at oral temperatures is a critical feature of the invention, for it is in this property that many of the disadvantages of previous approaches are overcome. The dissipative characteristic of liquid solutions is avoided since the compositions herein experience thickening at the site of treatment. Moreover, the problems of formulation, handling, delivery and application of viscous compositions are overcome since the present compositions may be free-flowing liquids prior to treatment.

A "semi-solid," as used herein, is a material whose physical state is between the solid and liquid state, in which pure or mixed solvent or solution is entrained within a network, and can alternatively be considered a gel. By "pure or mixed solvent and/or solution," as stated herein, it is recognized that a mixture of solvents may be absorbed by the network. Additionally, the solvent may include salts or other additives so as to form a solution, which may also be absorbed or entrained within the network.

"Thickening" as used herein, is where a composition undergoes a substantial increase in the viscosity of the composition. The degree of thickening is dependent on the initial viscosity of the composition.

As used herein, a "fine mist" or "aerosol" means fine droplets of a liquid sprayed into the air or, alternatively, a gaseous suspension of a fine liquid and/or colloidal particles In a preferred embodiment of the invention, the initial viscosity of the composition may be low enough such that the composition is in a liquid state. Subsequently, upon exposure to a temperature of about near or at oral temperature, the viscosity increases to result in a thickened composition. A viscosity increase in the range of about 10- to about 100-fold can be experienced when the initial viscosity is such that the composition is a liquid. Thus, for example, a composition in a liquid state may have a viscosity of about 0 to about 7000 poise. In response to an increase in temperature, the viscosity of the composition can increase to at least about 10,000 poise. Upon the lowering of the temperature, the composition preferably has the ability to reverse its viscosity and return to flow properties of a liquid.

The pre-treatment temperature is the temperature at which the composition is subjected to prior to application or treatment. The range for the pre-treatment temperature can be about 5° C. to about 29° C., although there may be certain instances where the temperature may be outside this range. Having a pre-treatment temperature at about 20° C. to about 25° C. allows the composition to be easily stored at ambient or room temperature. Alternatively, the compositions of the invention can also be advantageously stored at lower, refrigeration pre-treatment temperatures of about 5° C. to about 10° C. to provide improved stability and shelf life.

The treatment temperature is the temperature at which the composition is exposed to during intraoral application. This can be at or near body temperature, or about 30° C. to about 39° C.

In accordance with the invention, the dental composition consists of a water-miscible, physiologically compatible medium that is liquid at ambient temperature below about 30° C. and experiences thickening at oral temperatures above about 30° C. It has been found that a composition having a thickening transition temperature in the range of from about 25° C. to about 40° C. is useful in the practice of the present invention. Preferably, the thickening occurs in a temperature range of from about 25° C. to about 39° C., and more preferably from about 30° C. to about 35° C.

Compositions of this invention are comprised of water and one or more polymeric substances that provide the desired viscosity increase at the desired elevated temperature range in the composition. Optionally, adjuvants may be added to the composition. Preferably, the composition of this invention should be physiologically compatible so that no adverse reaction occurs if the dental composition comes in contact with human tissue or fluids.

As used herein, a "thermally responsive viscosity modifier" is one or more polymeric substances that provide the composition or polymeric system the capability of substantially changing its viscosity in response to a change in temperature. Suitable polymeric substances useful as thermally responsive viscosity modifiers include polyoxyalkylene polymers, particularly the polymeric surfactants available under the tradename PLURONIC. This class of polymers is available commercially from BASF Wyandotte Corporation. Other polyoxyalkylene polymers may also be useful as a thermally-responsive composition material.

A preferred dental composition in accordance with this invention comprises an aqueous solution of a selected polyoxyethylene-polyoxypropylene block copolymer. A composition comprising polyoxyethylene-polyoxypropylene block copolymers in which the number of polyoxyethylene units is at least about 50% of the number of units in the total molecule, and the block copolymer having an average molecular weight of from about 1100 to about 15,500 has been found to be particularly useful. It is more preferable that a composition comprises about 70% polyoxyethylene units of the total number of monomeric units in the copolymer and the copolymer has an average molecular weight of about 11,500. PLURONIC F-127 is a material that meets these criteria.

The PLURONIC polymers are closely related block copolymers that may be generically classified as polyoxypropylene-polyoxyethylene condensates that terminate in primary hydroxyl groups. These polymers are formed by the condensation of propylene oxide into a propylene glycol nucleus followed by the condensation of ethylene oxide onto both ends of the polyoxypropylene base. The polyoxyethylene hydrophilic groups on the ends of the base pre-polymer are controlled in length to constitute from about 10% to about 80% by weight of the final polymer.

The PLURONIC polymer series of products may be represented empirically by the formula: $HO(C_2H_4O)_a(C_3H_6O)_b(C_2H_4O)_cH$ where a and c are statistically equal.

The concentration of the block copolymers is an important parameter and can be formulated in such a manner corresponding to the other components' concentrations. By adjusting the concentration of the copolymer to accommodate other solutes present in the composition, any desired liquid to semi-solid transition temperature in the critical range of above ambient temperature and below body temperature can be achieved. Thus, the principal consideration is the selection of a concentration which, in conjunction with all of the constituents of the total composition, will provide a liquid to semi-solid transition temperature in the required range.

It has been found that a useful block copolymer concentration is from about 5% by weight to about 40% by weight (wt. %) of the composition, particularly from about 15% by weight to about 26% by weight of the composition. Excellent results have been obtained using aqueous solutions having from about 17% by weight to about 29% by weight of PLURONIC F-127. Increased polymer concentrations may be required in highly acidic systems to affect the same results as in a less acidic system so that, in optimizing the thickening or gelation characteristics for a system, the pH of the solution must be taken into account.

Particularly preferred polymers for the present invention are the PLURONIC F-127 and F-108. These viscosity modifiers are block copolymers of ethylene oxide and propylene oxide. Thickening tendencies of block copolymers increase as ethylene oxide content and total molecular weight increase. Thermally responsive block copolymers have been disclosed in U.S. Pat. Nos. 4,474,751; 4,474,752; 5,441,732; and 5,252,318, as well as the Product Catalog, "BASF Performance Chemicals," all the teachings of which are incorporated by reference herein. These block copolymers offer extremely low toxicity and a high degree of mildness for applications involving human contact.

The concentration of water in the composition can be in the range of from about 30% by weight to about 90% by weight of the composition. Preferably, water can exist in the range of about 40% by weight to about 80% by weight of the composition. The water used in forming the aqueous solution is preferably purified, as by distillation, filtration, ion-exchange, or the like.

Co-solvents may be used, including solutions comprising a polyol component such as propylene glycol or polyethylene glycol. Glycerin may also be used as a constituent of the composition.

The substantial moisture content of the compositions of the present invention provides the ability to easily deliver or apply a fine mist of a gel-on-contact aqueous material that provides substantial hydration of tissues that are subject to dehydration. By using a fine mist spray or aerosol delivery, it is possible to quickly and efficiently treat a relatively large surface area within the oral cavity with subsequent long-term retention upon gellation on the warm tissues. Of particular utility and interest is the ability to easily deliver hydrating solutions via a spray for treating xerostomia (dry mouth) wherein the compositions are readily retained for extended periods. Other benefits include a soothing and cooling effect due to the long-term evaporation of moisture, and the ability to protect sore, ulcerated, or burned tissues with a protective aqueous gel.

Optionally, adjuvants can be added to the composition for various purposes. Adjuvants may include active agents and additives. Active agents include, but are not limited to, whitening agents, fluoride sources, antimicrobials (e.g., antibacterials), enzymes (e.g., glucose oxidase, lactoperoxidase, and lysozymes), breath fresheners, local anesthetics, clotting agents, acid neutralizers (e.g., baking soda), cariostatic agents, bleaching agents, etching agents, medicaments, anti-calculus agents, and the like. Particularly useful active agents for delivery as a fine mist into the oral cavity include those for hydration of xerostomic patients (i.e., drymouth), prevention and treatment of halitosis (i.e., bad breath), treatment of periodontal disease, caries reduction, and oral coatings (optionally with local anesthetics) for irritated or ulcerated tissues such as canker sores or sore throat. Of particular interest are enzymes that include, for example, glucose oxidases and lactoperoxidases. Additives include, but are not limited to, fillers, flavorings, colorants, dyes, detection indicators (e.g., for caries, gingivitas, and the like), buffering agents, thixotropes, polyols, and the like. Additives may also be included in the composition to promote the stability of the formulation. Antimicrobial agents, antifungal agents, and preservatives may be added to the composition to improve shelf-life. Of particular interest is the application of aqueous compositions that remain localized at the desired site for extended time periods while providing the desired therapeutic effect. Especially significant is the ability to deliver thermally gellable aqueous liquids (optionally containing an adjuvant) to the oral cavity as a fine mist spray.

In the practice of the present invention, the oral cavity tissues that can be treated include human and animal soft and hard tissues. Soft tissues include for example, mucosal and gingival tissues. Hard tissues include, for example, teeth and their component parts (e.g., enamel, dentin, and cementum). The compositions disclosed in the present application may be applied to the oral environment as a fine mist or aerosol by any suitable means known in the art (e.g., U.S. Pat. No. 5,078,129). For example, the compositions may be placed in a spray bottle and delivered with a hand pump. Alternatively, the compositions may be placed in a container with a propellant (e.g., air, nitrogen, carbon dioxide, and hydrocarbons) and be delivered using a pressurized spray can. In either case, the composition is passed through a fine orifice to form the fine mist.

Examples of compositions that are useful by application as a fine mist in the oral environment are those including a peroxide. Dental compositions including a peroxide are useful in applications including, for example, those in which the peroxide serves as an antibacterial agent (e.g., treatment of halitosis, xerostomia, and oral infections) and the whitening of teeth. Preferred peroxides include hydrogen peroxide, carbamide peroxide ($CO(NH_2)_2H_2O_2$, a hydrogen peroxide urea complex), hydrogen peroxide salts (e.g., calcium salt and sodium salt), and combinations thereof. These peroxides are also known by alternative names, including urea hydrogen peroxide, hydrogen peroxide carbamide, or perhydrol-urea. Alternatively, sodium hypochlorite may be suitable in similar applications. Preferred concentrations of peroxide in the composition can vary depending upon its reactivity and intended use. With carbamide peroxide, for example, the preferred concentration for some applications is about 3% to about 40%, with about 4% to about 21% being most preferred. In the case of hydrogen peroxide, which is more reactive than carbamide peroxide, the preferred concentration for some applications is about 2% to about 10%.

Where the dental compositions are thermally reversible, the composition can be readily removed from the oral tissue by cooling the material below the liquid to semi-solid transition temperature, thus reversing the thickening effect. This can be accomplished with cool water or other physiologically compatible liquid. Alternatively, the concentrations of the components in the composition may be adjusted and diluted by adding water or other liquid solution. By adjusting the concentrations of the components, the transition temperature is correspondingly adjusted, and thus provides the user the ability to remove the composition even with warm solutions. Water or other liquid solutions may be administered through a rinsing cup, squirt bottle, a liquid dispensing dental tool, spray pump, aerosol, or any other liquid dispensing device that can provide solution to the oral environment. Preferably, administering cool or cold water provides a significant decrease in viscosity. Alternatively, the gelled composition may be brushed, wiped, or blown off.

These and other aspects of the invention are illustrated by the following examples, which should not be viewed as limiting in scope. Unless otherwise indicated, all molecular weights are number average molecular weights and all ratios, parts and percentages are by weight.

EXAMPLES

Preparation of Stock Solution 1

An aqueous stock solution containing approximately 15% hydrogen peroxide($H_2O_2$) was prepared by transferring 5 grams of a 30% $H_2O_2$ (J. T. Baker) and 5 grams of distilled water to a glass vial. The stock solution was mixed thoroughly.

Preparation of Stock Solution 2

An aqueous stock solution containing approximately 20% urea hydrogen peroxide (carbamide peroxide) was prepared by transferring 4 grams of 97% urea hydrogen hydrogen peroxide (Sigma) and 16 grams of distilled water to a glass vial. The stock solution was mixed thoroughly. (The hydrogen peroxide content of the urea hydrogen peroxide was about 35%). Stock solution contained about 7% $H_2O_2$.

Preparative Example 1

A thermally-reversible hydrogen peroxide composition was prepared by transferring the ingredients below to a glass vial and mixing thoroughly until a colorless and transparent liquid solution was obtained.

| | |
|---|---|
| Stock Solution 1 | 1.60 grams |
| PLURONIC F127 (BASF) | 0.40 grams |
| | 2.00 grams |

The above solution contained approximately 12% hydrogen peroxide, 68% water and 20% PLURONIC F127. The glass vial containing the liquid peroxide solution was warmed to body temperature by holding the vial in a human hand. Following about one to two minutes, the liquid was transformed into a colorless, transparent composition that did not flow upon inverting the vial. The vial was allowed to cool to room temperature wherein the composition was transformed back to the low viscosity state. This cycle was repeated several times with the same outcome.

The liquid and semi-solid (gel) states were both semi-quantitatively evaluated for hydrogen peroxide utilizing hydrogen peroxide analysis strips. The analysis utilized "EM Quant Peroxide Test Strips" (EM Science Gibbstown, N.J., Catalog No. 10011-1). The compositions were evaluated according to the manufacturer's directions.

Results of the tests indicated that both the liquid and semi-solid states contained significant amounts of available peroxide.

The same sample was re-evaluated 2 months later and found to still exhibit thermally-reversible characteristics and comparable hydrogen peroxide levels based on the semi-quantitative analysis.

Preparative Example 2

A thermally reversible composition containing urea hydrogen peroxide was prepared by transferring the ingredients below to a glass vial and mixing thoroughly until a colorless and transparent liquid solution was obtained.

| | |
|---|---|
| Stock Solution 2 | 4.00 grams |
| PLURONIC F127 (BASF) | 1.00 grams |
| | 5.00 grams |

The above solution contained approximately 16% urea hydrogen peroxide (or about 5.6% hydrogen peroxide), 64% water and 20% PLURONIC F127. The glass vial containing the liquid peroxide solution was warmed to body temperature by holding the vial in a human hand. After about 1 minute, the liquid transformed to a colorless, transparent composition that did not flow upon inverting the vial. The vial was allowed to cool to room temperature wherein the semi-solid composition was transformed back to the low viscosity state. This cycle was repeated several time with the same outcome.

The liquid and semi-solid states were both semi-quantitatively evaluated for hydrogen peroxide utilizing hydrogen peroxide analysis strips, EM Quant Peroxide Test Strips (EM Science; Gibbstown, N.J., Catalog No. 10011-1), according to the manufacturer's directions. Both the liquid and semi-solid states indicated the presence of significant amounts of available peroxide.

The same sample was re-evaluated 9 days later and found to still exhibit thermally-reversible characteristics and comparable hydrogen peroxide levels based on the semi-quantitative analysis.

Table 1 summarizes the results of the two previous examples. The "+"indicates an increase in the viscosity. The "−" indicates a decrease in the viscosity. The presence of hydrogen peroxide as indicated in the table are the results obtained from the semi-quantitative test using the EM Quant Peroxide Test Strips and test method.

TABLE 1

| | % Peroxide | 35° C. viscosity | 35° C. viscosity @9 days | 25° C. viscosity | 25° C. viscosity @9 days | $H_2O_2$ Present | $H_2O_2$ Present @9 days |
|---|---|---|---|---|---|---|---|
| Preparative Example 1 | 12 | + | + | − | − | Yes | Yes |
| Preparative Example 2 | 16 | + | + | − | − | Yes | Yes |

Preparative Example 3

Several compositions were evaluated for viscosity as a function of temperature. The compositions are described below:

TABLE 2

Comparative Sample A

| Component | parts by weight (g) | % by weight | Physical Appearance at 23° C. | Physical Appearance at body temp |
|---|---|---|---|---|
| Urea hydrogen peroxide | 20 | 20 | Low viscosity, colorless liquid | Low viscosity, Colorless liquid |
| Water | 80 | 80 | | |

TABLE 3

Sample B

| Component | Parts by weight (g) | % by weight | Physical Appearance at 23° C. | Physical Appearance at Body temp |
|---|---|---|---|---|
| Urea hydrogen peroxide | 20 | 16 | Low viscosity, Colorless liquid | non-flowing, colorless gel |
| Water | 80 | 64 | | |
| PLURONIC F-127 | 25 | 20 | | |

TABLE 4

Sample C

| Component | Parts by weight (g) | % by weight | Physical Appearance at 23° C. | Physical Appearance at body temp |
|---|---|---|---|---|
| Urea hydrogen peroxide | 1.6 | 14.7 | Non-flowing, colorless gel | Non-flowing, colorless gel |
| Water | 6.4 | 58.7 | | |
| PLURONIC F-127 | 2.0 | 18.3 | | |
| CAB-O-SIL M-5* (fumed silica) | 0.9 | 8.3 | | |

*available from Cabot Corp. (Boston, MA)

Samples were further evaluated for viscosity as a function of temperature between 15° C. and 45° C. utilizing a Rheometrics RDA II Rheometer. Complex viscosity,. $\eta^*$ (units of measure is in Poise), versus temperature data were obtained using a controlled strain rheometer ("RDA2", Rheometrics Scientific, Piscataway, N.J.). A parallel plate geometry was used with a plate diameter of 25 mm and a gap of approximately 1 mm. Samples were subjected to an oscillatory strain of 10% applied at a frequency of 1 rad/sec while the temperature was ramped from 15° C. and 45° C. (3° C./min).

Set out below is the RDA viscosity data. FIG. 1 illustrates that aqueous compositions containing PLURONIC F127 polymer exhibit a relatively sharp increase in viscosity upon warming from room temperature to about 45° C. Sample C, which exhibited semi-solid-like characteristics at room temperature (due to the incorporation of a fumed silica), also increased substantially upon an increase in temperature.

TABLE 5

| A | | B | | C | |
|---|---|---|---|---|---|
| Temp °C. | $\eta^*$ P | Temp °C. | $\eta^*$ P | Temp °C. | $\eta^*$ P |
| 14.02 | 9.75424 | 17.88 | 2308.56 | 18.5 | 52951.5 |
| 14.28 | 3.35258 | 17.88 | 2379.72 | 18.3 | 42757.9 |
| 15.36 | 7.33292 | 18.54 | 2587.46 | 18.79 | 41559.9 |
| 17.28 | 3.46242 | 19.42 | 3111.41 | 19.64 | 41144.7 |
| 19.46 | 5.85152 | 20.91 | 3711.59 | 20.76 | 41347.4 |
| 21.12 | 5.79953 | 22.36 | 4580.71 | 22.09 | 42047 |
| 22.89 | 7.09599 | 23.72 | 5661.42 | 23.51 | 43615.7 |
| 24.91 | 4.19887 | 25.46 | 7221.65 | 24.04 | 45494.3 |
| 26.31 | 0.87001 | 26.85 | 8940.38 | 26.03 | 48768.7 |
| 28.23 | 3.13629 | 28.73 | 25375.6 | 27.94 | 55250.6 |
| 30.12 | 4.57411 | 30.7 | 29698.2 | 29.57 | 82062.6 |
| 31.6 | 4.7215 | 32.07 | 33651.8 | 31.31 | 94988.5 |
| 33.2 | 9.01765 | 33.57 | 37181.2 | 32.83 | 1.04E+05 |
| 35.02 | 8.0025 | 35.22 | 40557.8 | 34.36 | 1.09E+05 |
| 36.75 | 2.94618 | 36.89 | 43766.3 | 36.09 | 1.13E+05 |
| 38.44 | 4.24626 | 38.43 | 46677.4 | 37.49 | 1.20E+05 |
| 40.85 | 1.08273 | 40.01 | 49322.7 | 38.95 | 1.26E+05 |
| 42.92 | 5.04081 | 41.84 | 52296.6 | 40.7 | 1.32E+05 |
| | | 43.52 | 54490.4 | 42.2 | 1.36E+05 |
| | | | | 43.9 | 1.39E+05 |

Example 1

An oral hydration composition containing 18 parts PLURONIC F127 and 82 parts water was prepared by combining and thoroughly mixing the ingredients at approximately 5° C. The resultant homogeneous composition was a liquid at between 5° C. and room temperature (e.g., about 25° C.). The liquid was transferred to a vial fitted with hand pumped aerosol dispenser. The composition was easily dispensed as a fine mist at room temperature. The composition was sprayed onto a human hand wherein the spray gelled instantaneously on the tissue. In a similar manner, the gel could also be sprayed as a fine mist onto a surface in the oral environment. The hydrogel composition remained an immobile gel and provided a cooling effect over time. A similar, water-only solution was similarly sprayed onto the human hand wherein the liquid flowed and failed to remain localized.

Example 2

An oral fluoride composition containing 18 parts PLURONIC F127, 90 parts water and 1 part sodium fluoride was prepared by combining and thoroughly mixing the ingredients at approximately 5° C. The resultant homogeneous composition was a liquid at between 5° C. and room temperature (e.g., about 25° C.). The liquid is transferred to a vial fitted with hand pumped aerosol dispenser. The composition is easily dispensed as a fine mist at room temperature. The composition is sprayed onto an artificial tooth heated to about 37° C. wherein it forms an immobile gel on contact with the tooth. Alternatively, the liquid can be sprayed onto a tooth or into an oral cavity as a fine mist.

Example 3

An anti-bacterial, enzymatic oral hydration composition for xerostomic applications was prepared by combining 2.4 parts mouthwash available under the trade designation BIOTENE from Laclede Research Laboratories (Rancho Dominguez, Calif., and containing lysozyme, lactoferrin, glucose oxidase, lactoperoxidase, water, xylitol, hydrogenated starch, propylene glycol, hydroxyethyl cellulose, aloe vera, peppermint, poloxamer 407, calcium lactate, sodium benzoate and benzoic acid), 0.9 parts PLURONIC F127, and 2.5 parts water and thoroughly mixing the ingredients at approximately 5° C. The resultant homogeneous composition was a liquid at between 5° C. and room temperature (e.g., about 25° C.). The liquid is transferred to a vial fitted with hand pumped aerosol dispenser. The composition is easily dispensed as a fine mist at room temperature. The composition is sprayed onto an artificial tooth heated to about 37° C. wherein it forms an immobile gel on contact with the tooth. Alternatively, the liquid can be sprayed onto a tooth or into an oral cavity as a fine mist.

Example 4

An oral liquid composition containing 18 parts PLURONIC F127, 82 parts water and 1 part sodium bicarbonate (baking soda) was prepared by combining and thoroughly mixing the ingredients at approximately 5° C. The resultant homogeneous composition was a liquid at between 5° C. and room temperature (e.g., about 25° C.). The liquid is transferred to a vial fitted with hand pumped aerosol dispenser. The composition is easily dispensed as a fine mist at room temperature. The composition is sprayed onto an artificial tooth heated to about 37° C. wherein it forms an immobile gel on contact with the tooth. Alternatively, the liquid can be sprayed onto a tooth or into an oral cavity as a fine mist.

What is claimed is:

1. A method of applying a dental composition in the oral environment using an aqueous dental composition comprising about 10% by weight to about 50% by weight of a thermally responsive viscosity modifier and water, wherein the composition is in a low viscosity state at a pre-treatment temperature and a highly viscous state at a treatment temperature that is higher than the pre-treatment temperature, comprising:

spraying the composition as a fine mist onto a surface, wherein the composition is at the pretreatment temperature and in the low viscosity state prior to being sprayed onto the surface, allowing the composition to warm to the treatment temperature and increase in viscosity to the highly viscous state wherein the viscosity of the composition at the treatment temperature is at least about 10 times the viscosity of the composition at the pre-treatment temperature, and allowing the composition to remain on the surface.

2. The method of claim 1 wherein the pre-treatment temperature is at most about room temperature.

3. The method of claim 1 wherein the treatment temperature is about body temperature.

4. The method of claim 1 wherein the thermally responsive viscosity modifier is a polyoxyalkylene polymer.

5. The method of claim 1 wherein the viscosity of the composition at the treatment temperature is about 10 times to about 100 times the viscosity of the composition at the pre-treatment temperature.

6. The method of claim 1 wherein the composition decreases in viscosity upon cooling from the treatment temperature.

7. The method of claim 6 further comprising removing the composition from the surface by cooling the composition from the treatment temperature.

8. The method of claim 7 wherein the composition is cooled by application of a cool liquid.

9. The method of claim 8 wherein the liquid comprises water.

10. The method of claim 1 wherein spraying the composition onto a surface comprises spraying the composition onto hard tissue.

11. The method of claim 1 wherein spraying the composition onto a surface comprises spraying the composition onto soft tissue.

12. The method of claim 11 wherein allowing the composition to remain on the surface hydrates the surface.

13. The method of claim 1 wherein the dental composition comprises about 17% by weight to about 40% by weight of a thermally responsive viscosity modifier.

14. The method of claim 1 wherein the composition further comprises an adjuvant.

15. The method of claim 14 wherein the adjuvant is selected from the group consisting of acids, peroxides, fluoride sources, medicaments, stability promotors, acid neutralizers, preservatives, adhesive modifiers, fillers, dyes, flavorings, sweeteners, saliva inducers, and breath fresheners.

16. The method of claim 14 wherein the adjuvant is selected from the group consisting of anti-microbial agents, anti-calculus agents, anti-fungal agents, cariostatic agents, local anesthetics, enzymes, and sodium bicarbonate.

17. The method of claim 1 wherein the composition further comprises a propellant.

18. The method of claim 1 wherein the aqueous composition further comprises a salt.

* * * * *

UNITED STATES PATENT AND TRADEMARK OFFICE
CERTIFICATE OF CORRECTION

PATENT NO.   : 6,620,405 B2
DATED        : September 16, 2003
INVENTOR(S)  : Oxman, Joel D.

It is certified that error appears in the above-identified patent and that said Letters Patent is hereby corrected as shown below:

Column 1,
Line 22, please delete "it" and insert in place thereof -- its --.
Line 36, please delete "non-homogenous" and insert in place thereof -- non-homogeneous --.

Column 2,
Line 11, please insert -- is -- following "most".
Line 15, please delete "promotors" and insert in place thereof -- promoters --.

Column 5,
Line 8, please delete "affect" and insert in place thereof -- effect --.

Column 6,
Line 3, please delete "gingiritas" and insert in place thereof -- gingivitus --.

Column 7,
Line 20, please delete the second occurrence of "hydrogen".

Column 8,
Line 32, please delete "time" and insert in place thereof -- times --.

Column 12,
Line 34, please delete "promotors" and insert in place thereof -- promoters --.

Signed and Sealed this

Twenty-seventh Day of July, 2004

JON W. DUDAS
*Acting Director of the United States Patent and Trademark Office*